(12) United States Patent
Carbunaru

(10) Patent No.: US 9,339,655 B2
(45) Date of Patent: May 17, 2016

(54) SYSTEM AND METHOD FOR COMPOUNDING LOW-FREQUENCY SOURCES FOR HIGH-FREQUENCY NEUROMODULATION

(71) Applicant: BOSTON SCIENTIFIC NEUROMODULATION CORPORATION, Valencia, CA (US)

(72) Inventor: Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/931,090

(22) Filed: Jun. 28, 2013

(65) Prior Publication Data

US 2014/0005753 A1    Jan. 2, 2014

Related U.S. Application Data

(60) Provisional application No. 61/666,833, filed on Jun. 30, 2012.

(51) Int. Cl.
*A61N 1/36* (2006.01)
*A61N 1/39* (2006.01)
*A61N 1/362* (2006.01)

(52) U.S. Cl.
CPC .......... *A61N 1/36189* (2013.01); *A61N 1/3605* (2013.01); *A61N 1/362* (2013.01); *A61N 1/36003* (2013.01); *A61N 1/3606* (2013.01); *A61N 1/36007* (2013.01); *A61N 1/36171* (2013.01); *A61N 1/36178* (2013.01); *A61N 1/3956* (2013.01)

(58) Field of Classification Search
CPC .......... A61N 1/36189; A61N 1/36178; A61N 1/36171
USPC .......................................... 607/46, 66, 68–70
See application file for complete search history.

(56) References Cited

U.S. PATENT DOCUMENTS

| | | | |
|---|---|---|---|
| 5,603,726 A * | 2/1997 | Schulman et al. | 607/57 |
| 6,289,247 B1 * | 9/2001 | Faltys et al. | 607/57 |

(Continued)

FOREIGN PATENT DOCUMENTS

| | | |
|---|---|---|
| WO | WO-2006029257 A2 | 3/2006 |
| WO | WO-2006135791 A2 | 12/2006 |

(Continued)

OTHER PUBLICATIONS

PCT International Search Report for PCT/US2013/048686, Applicant: Boston Scientific Neuromodulation Corporation, Form PCT/ISA/210 and 220, dated Oct. 15, 2013 (9pages).

(Continued)

*Primary Examiner* — George Evanisko
(74) *Attorney, Agent, or Firm* — Schwegman Lundberg & Woessner, P.A.

(57) ABSTRACT

A neuromodulation system and method of providing therapy to a patient. A plurality of individual electrical pulse trains is generated at a respective plurality of individual pulse rates. The plurality of individual electrical pulse trains are concurrently respectively from a plurality of electrodes to a common electrode via tissue of the patient, thereby creating a combined electrical pulse train having an average pulse rate equal to or greater than 1 KHz.

20 Claims, 10 Drawing Sheets

(56) References Cited

U.S. PATENT DOCUMENTS

| | | | |
|---|---|---|---|
| 6,516,227 B1 | 2/2003 | Meadows et al. | |
| 6,675,046 B2 | 1/2004 | Holsheimer | |
| 6,895,280 B2 * | 5/2005 | Meadows et al. | 607/46 |
| 6,993,384 B2 | 1/2006 | Bradley et al. | |
| 7,317,948 B1 | 1/2008 | King et al. | |
| 7,333,857 B2 | 2/2008 | Campbell | |
| 7,539,538 B2 | 5/2009 | Parramon et al. | |
| 7,650,184 B2 | 1/2010 | Walter | |
| 7,979,133 B2 | 7/2011 | Feler et al. | |
| 8,019,439 B2 | 9/2011 | Kuzma et al. | |
| 8,170,675 B2 | 5/2012 | Alataris et al. | |
| 8,209,021 B2 | 6/2012 | Alataris et al. | |
| 8,224,453 B2 | 7/2012 | De Ridder | |
| 8,255,057 B2 | 8/2012 | Fang et al. | |
| 8,355,797 B2 | 1/2013 | Caparso et al. | |
| 8,359,102 B2 | 1/2013 | Alataris et al. | |
| 8,359,103 B2 | 1/2013 | Alataris et al. | |
| 8,396,559 B2 | 3/2013 | Alataris et al. | |
| 8,423,147 B2 | 4/2013 | Alataris et al. | |
| 8,455,716 B2 | 6/2013 | Huang et al. | |
| 8,504,147 B2 | 8/2013 | Deem et al. | |
| 8,615,300 B2 | 12/2013 | Feler et al. | |
| 8,649,874 B2 | 2/2014 | Alataris et al. | |
| 8,670,831 B2 | 3/2014 | Wacnik et al. | |
| 8,676,329 B2 | 3/2014 | Wacnik et al. | |
| 8,676,331 B2 | 3/2014 | Parker | |
| 8,731,675 B2 | 5/2014 | Ranu et al. | |
| 8,751,009 B2 | 6/2014 | Wacnik | |
| 2003/0139781 A1 | 7/2003 | Bradley et al. | |
| 2004/0034394 A1 | 2/2004 | Woods et al. | |
| 2005/0267546 A1 | 12/2005 | Parramon et al. | |
| 2006/0149337 A1 | 7/2006 | John | |
| 2007/0142874 A1 | 6/2007 | John | |
| 2007/0150036 A1 | 6/2007 | Anderson | |
| 2007/0168004 A1 | 7/2007 | Walter | |
| 2007/0168007 A1 | 7/2007 | Kuzma et al. | |
| 2008/0188909 A1 | 8/2008 | Bradley | |
| 2009/0204173 A1 | 8/2009 | Fang et al. | |
| 2010/0010566 A1 | 1/2010 | Thacker et al. | |
| 2010/0023090 A1 | 1/2010 | Jaax et al. | |
| 2010/0114196 A1 | 5/2010 | Burnes et al. | |
| 2010/0121409 A1 | 5/2010 | Kothandaraman et al. | |
| 2010/0152817 A1 | 6/2010 | Gillbe | |
| 2010/0249875 A1 | 9/2010 | Kishawi et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2010/0324630 A1 | 12/2010 | Lee et al. | |
| 2011/0054568 A1 | 3/2011 | Lane et al. | |
| 2011/0054570 A1 | 3/2011 | Lane | |
| 2011/0184486 A1 | 7/2011 | De Ridder | |
| 2011/0184488 A1 | 7/2011 | De Ridder | |
| 2011/0201977 A1 * | 8/2011 | Tass | 601/15 |
| 2012/0016437 A1 | 1/2012 | Alataris et al. | |
| 2012/0059446 A1 | 3/2012 | Wallace et al. | |
| 2012/0083709 A1 | 4/2012 | Parker et al. | |
| 2012/0203304 A1 | 8/2012 | Alataris et al. | |
| 2012/0253422 A1 | 10/2012 | Thacker et al. | |
| 2012/0265279 A1 | 10/2012 | Zhu et al. | |
| 2012/0283797 A1 | 11/2012 | De Ridder | |
| 2012/0290041 A1 | 11/2012 | Kim et al. | |
| 2013/0041425 A1 | 2/2013 | Fang et al. | |
| 2013/0066411 A1 | 3/2013 | Thacker et al. | |
| 2013/0116752 A1 | 5/2013 | Parker et al. | |
| 2013/0131760 A1 | 5/2013 | Rao | |
| 2013/0268021 A1 | 10/2013 | Moffitt | |
| 2013/0296975 A1 | 11/2013 | Lee et al. | |
| 2014/0081349 A1 | 3/2014 | Lee et al. | |
| 2014/0364920 A1 | 12/2014 | Doan et al. | |

FOREIGN PATENT DOCUMENTS

| | | |
|---|---|---|
| WO | WO-2008095185 A1 | 8/2008 |
| WO | WO-2014197596 A1 | 12/2014 |

OTHER PUBLICATIONS

PCT Written Opinion of the International Search Authority for PCT/US2013/048686, Applicant: Boston Scientific Neuromodulation Corporation, Form PCT/ISA/237, dated Oct. 15, 2013 (8pages).

"U.S. Appl. No. 13/843,102, Advisory Action mailed Feb. 10, 2014", 3 pgs.

"U.S. Appl. No. 13/843,102, Appeal Brief filed Apr. 16, 2014", 16 pgs.

"U.S. Appl. No. 13/843,102, Examiner Interview Summary mailed Oct. 7, 2013", 3 pgs.

"U.S. Appl. No. 13/843,102, Examiner Interview Summary mailed Nov. 18, 2014", 3 pgs.

"U.S. Appl. No. 13/843,102, Final Office Action mailed Sep. 29, 2014", 8 pgs.

"U.S. Appl. No. 13/843,102, Final Office Action mailed Dec. 13, 2013", 7 pgs.

"U.S. Appl. No. 13/843,102, Non Final Office Action mailed Jun. 10, 2014", 11 pgs.

"U.S. Appl. No. 13/843,102, Notice of Allowance mailed Dec. 5, 2014", 8 pgs.

"U.S. Appl. No. 13/843,102, Preliminary Amendment filed Jul. 5, 2013", 5 pgs.

"U.S. Appl. No. 13/843,102, Response filed Feb. 4, 2014 to Final Office Action mailed Dec. 13, 2013", 9 pgs.

"U.S. Appl. No. 13/843,102, Response filed Aug. 25, 2014 to Non Final Office Action mailed Jun. 10, 2014", 9 pgs.

"U.S. Appl. No. 13/843,102, Response filed Nov. 11, 2013 to Non Final Office Action mailed Oct. 15, 2013", 8 pgs.

"U.S. Appl. No. 13/843,102, Response filed Nov. 19, 2014 to Final Office Action mailed Sep. 29, 2014", 10 pgs.

"International Application Serial No, PCT/US2014/40910, International Search Report mailed Sep. 19, 2014", 4 pgs.

"International Application Serial No. PCT/US2014/40910, Written Opinion mailed Sep. 19, 2014", 6 pgs.

"Posterior horn of spinal cord", Wikipedia, [Online] retrieved from the internet: <http://en.wikipedia.org/wiki/Posterior_horn_of_spinal_cord>, (Jul. 22, 2013), 1 pgs.

Bradley, Kerry, et al., "Method for Epidural Stimulation of Neural Structures", U.S. Appl. No. 61/704,381, filed Sep. 21, 2012, 45 pgs.

Rao, Prakash, et al., "Technique for Linking Electrodes Together During Programming of Neurostimulation System", U.S. Appl. No. 61/561,760, filed Nov. 18, 2011

Vansickle, Dennis Allen, et al., "Neuromodulation System and Method for Transitioning Between Programming Modes", U.S. Appl. No. 14/214,752, filed Mar. 2014.

Vansickle, Dennis Allen, "Systems and Methods for Delivering Sub-Threshold Therapy to a Patient", U.S. Appl. No. 61/801,917, filed Mar. 15, 2013.

* cited by examiner

SYSTEM AND METHOD FOR COMPOUNDING LOW-FREQUENCY SOURCES FOR HIGH-FREQUENCY NEUROMODULATION

RELATED APPLICATION DATA

The present application claims the benefit under 35 U.S.C. §119 to U.S. provisional patent application Ser. No. 61/666,833, filed Jun. 30, 2012. The foregoing application is hereby incorporated by reference into the present application in its entirety.

FIELD OF THE INVENTION

The present invention relates to tissue modulation systems, and more particularly, to a system and method for delivering high-frequency neuromodulation electrical energy to provide therapy.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of spinal modulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neuromodulation systems typically includes one or more electrode carrying modulation leads, which are implanted at the desired stimulation site, and a neuromodulation device implanted remotely from the stimulation site, but coupled either directly to the neuromodulation lead(s) or indirectly to the neuromodulation lead(s) via a lead extension. Thus, electrical pulses can be delivered from the neuromodulation device to the electrode(s) to activate a volume of tissue in accordance with a set of modulation parameters and provide the desired efficacious therapy to the patient. In particular, electrical energy conveyed between at least one cathodic electrode and at least one anodic electrode creates an electrical field, which when strong enough, depolarizes (or "stimulates") the neurons beyond a threshold level, thereby inducing the firing of action potentials (APs) that propagate along the neural fibers. A typical modulation parameter set may include the electrodes that are sourcing (anodes) or returning (cathodes) the modulating current at any given time, as well as the amplitude, duration, and rate of the stimulation pulses.

The neuromodulation system may further comprise a handheld patient programmer to remotely instruct the neuromodulation device to generate electrical stimulation pulses in accordance with selected modulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

Of course, neuromodulation devices are active devices requiring energy for operation, and thus, the neuromodulation system may oftentimes includes an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be used to directly power the electronic componentry contained within the neuromodulation device, or can be stored in a rechargeable battery within the neuromodulation device, which can then be used to power the electronic componentry on-demand.

Typically, the therapeutic effect for any given neuromodulation application may be optimized by adjusting the modulation parameters. Often, these therapeutic effects are correlated to the diameter of the nerve fibers that innervate the volume of tissue to be modulated. For example, in SCS, activation (i.e., recruitment) of large diameter sensory fibers is believed to reduce/block transmission of smaller diameter pain fibers via interneuronal interaction in the dorsal horn of the spinal cord. Activation of large sensory fibers also typically creates a sensation known as paresthesia that can be characterized as an alternative sensation that replaces the pain signals sensed by the patient.

Although alternative or artifactual sensations are usually tolerated relative to the sensation of pain, patients sometimes report these sensations to be uncomfortable, and therefore, they can be considered an adverse side-effect to neuromodulation therapy in some cases. It has been shown that high-frequency pulsed electrical energy can be effective in providing neuromodulation therapy for chronic pain without causing paresthesia. In contrast to conventional neuromodulation therapies, which employ low- to mid-frequencies to provide a one-to-one correspondence between the generation of an AP and each electrical pulse, high frequency modulation (e.g., 1 KHz-50 KHz) can be employed to block naturally occurring APs within neural fibers or otherwise disrupt the APs within the neural fibers. Although high-frequency modulation therapies have shown good efficacy in early studies, it would be desirable to provide high-frequency modulation therapy using already existing lower frequency sources.

There, thus, remains a need to decrease the energy requirements for high-frequency neuromodulation therapy.

SUMMARY OF THE INVENTION

In accordance with one aspect of the present inventions, a neuromodulation system comprises a plurality of electrical terminals configured for being coupled to a respective plurality of electrodes, and modulation output circuitry configured for respectively generating a plurality of individual electrical pulse trains (which may include monophasic pulses or multiphasic pulses) at a plurality of pulse rates. In one embodiment, the modulation output circuitry comprises a single electrical source for generating the plurality of electrical pulse trains. In another embodiment, the modulation output circuitry comprises a plurality of electrical sources for respectively generating the plurality of electrical pulse trains.

The modulation output circuitry may be configured for generating at least two of the plurality of individual electrical pulse trains in accordance with different values of a modulation parameter that comprises one of a pulse amplitude, pulse duration, and pulse shape. The neuromodulation system further comprises a switching network coupled between the plurality of electrical terminals and the modulation output circuitry. At least two of the plurality of pulse rates may be identical to each other or may differ from each other.

The neuromodulation system further comprises control circuitry configured for operating the switching network to concurrently convey the plurality of electrical pulse trains respectively from a plurality of electrical terminals to a common electrical terminal, thereby creating a combined electrical pulse train having an average pulse rate equal to or greater than 1 KHz. The average pulse rate may be equal to the sum of the plurality of pulse rates. In one embodiment, the average pulse rate is less than 50 KHz. The combined electrical pulse train at the common electrical terminal may be anodic.

The control circuitry may be configured for operating the switching network without arbitration, such that the pulses of each respective individual electrical pulse train are uniformly spaced from each other. Or the control circuitry maybe configured for operating the switching network with arbitration, such that the pulses of at least one of the plurality of individual electrical pulse trains are variably spaced from each other in a manner that limits the time intervals between the pulses of the combined electrical pulse train to a minimum time interval. In one embodiment, the control circuitry is configured for instructing the modulation output circuitry to generate each of the individual electrical pulse trains in accordance with a cyclically varying set of modulation parameters. In another embodiment, the control circuitry is configured for instructing the modulation output circuitry to repeatedly generate the plurality of individual electrical pulse trains in a bursting pattern.

In an optional embodiment, the modulation output circuitry is further configured for generating another plurality of individual electrical pulse trains at another respective plurality of pulse rates, and the control circuitry is further configured for operating the switching network to concurrently convey the other plurality of individual electrical pulse trains respectively from another plurality of electrical terminals to another common electrical terminal, thereby creating another combined electrical pulse train having another average pulse rate greater than 1 KHz.

In another optional embodiment, the neuromodulation system further comprises a user interface configured for receiving an input from a user specifying the electrode corresponding to the common electrical terminal, in which case, the control circuitry may be configured for selecting the common electrical terminal in response to the input from the user specifying the electrode corresponding to the common electrical terminal. The control circuitry may also be configured for automatically selecting the plurality of electrical terminals in response to the input from the user specifying the electrode corresponding to the common electrical terminal.

In another embodiment, the user interface is further configured for receiving an input from the user specifying electrodes corresponding to the plurality of electrical terminals, in which case, the control circuitry may be configured for selecting the plurality of electrical terminals in response to the user input specifying the electrodes corresponding to the plurality of electrical terminals. In still another embodiment, the user interface is further configured for receiving an input from the user specifying an electrode corresponding to an electrical terminal, in which case, the control circuitry may be configured for selecting the plurality of electrical terminals that does not include the electrical terminal in response to the user input specifying the electrode corresponding to the electrical terminal.

In accordance with a second aspect of the present inventions, a method of providing therapy to a patient is provided. The method comprises generating a plurality of electrical pulse trains (which may include monophasic pulses or multiphasic pulses) at a respective plurality of pulse rates. At least two of the plurality of individual electrical pulse trains may be generated in accordance with different values of a modulation parameter that comprises one of a pulse amplitude, pulse duration, and pulse shape. At least one pulse in each of the plurality of individual electrical pulse trains is multiphasic. At least two of the plurality of pulse rates may be identical to each other or may differ from each other.

The method further comprises concurrently conveying the plurality of electrical pulse trains respectively from a plurality of electrodes to a common electrode via tissue of the patient, thereby creating a combined electrical pulse train having an average pulse rate equal to or greater than 1 KHz. The average pulse rate may be equal to the sum of the plurality of pulse rates. In one method, the average pulse rate is less than 50 KHz. In another method, the tissue adjacent the common electrode is therapeutically modulated by the combined electrical pulse train to provide the therapy, whereas the tissue adjacent the plurality of electrodes is not therapeutically modulated by the plurality of electrical pulse trains.

In one method, the conveyance of the plurality of individual electrical pulse trains is not arbitrated, such that the pulses of each respective individual electrical pulse trains are uniformly spaced from each other. In another method, the conveyance of the plurality of individual electrical pulse trains is not arbitrated, such that the pulses of at least one of the plurality of individual pulse trains are variably spaced from each other in a manner that limits the time intervals between the pulses of the combined electrical pulse train to a minimum time interval. Each of the individual electrical pulse trains may be generated in accordance with a cyclically varying set of modulation parameters and/or plurality of individual electrical pulse trains may be repeatedly generated in a bursting pattern.

An optional method further comprises generating another plurality of individual electrical pulse trains at another respective plurality of pulse rates, and concurrently conveying the other plurality of individual electrical pulse trains respectively from another plurality of electrodes to another common electrode, thereby creating another combined electrical pulse train having another an average pulse rate greater than any of the other plurality of pulse rates.

Another optional method further comprises receiving an input from a user specifying the common electrode, and selecting the common electrode in response to the input from the user specifying the common electrode. The optional method may comprise automatically selecting the plurality of electrodes in response to the input from the user specifying the common electrode. Or the optional method may comprise receiving an input from the user specifying electrodes corresponding to the plurality of electrodes, and selecting the plurality of electrodes in response to the user input specifying the plurality of electrodes. Another method comprises receiving an input from the user specifying an electrode, and selecting the plurality of electrodes that does not include the electrode in response to the user input specifying the electrode.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord modulation (SCM) system. However, it is to be understood that the while the invention lends itself well to applications in SCM, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
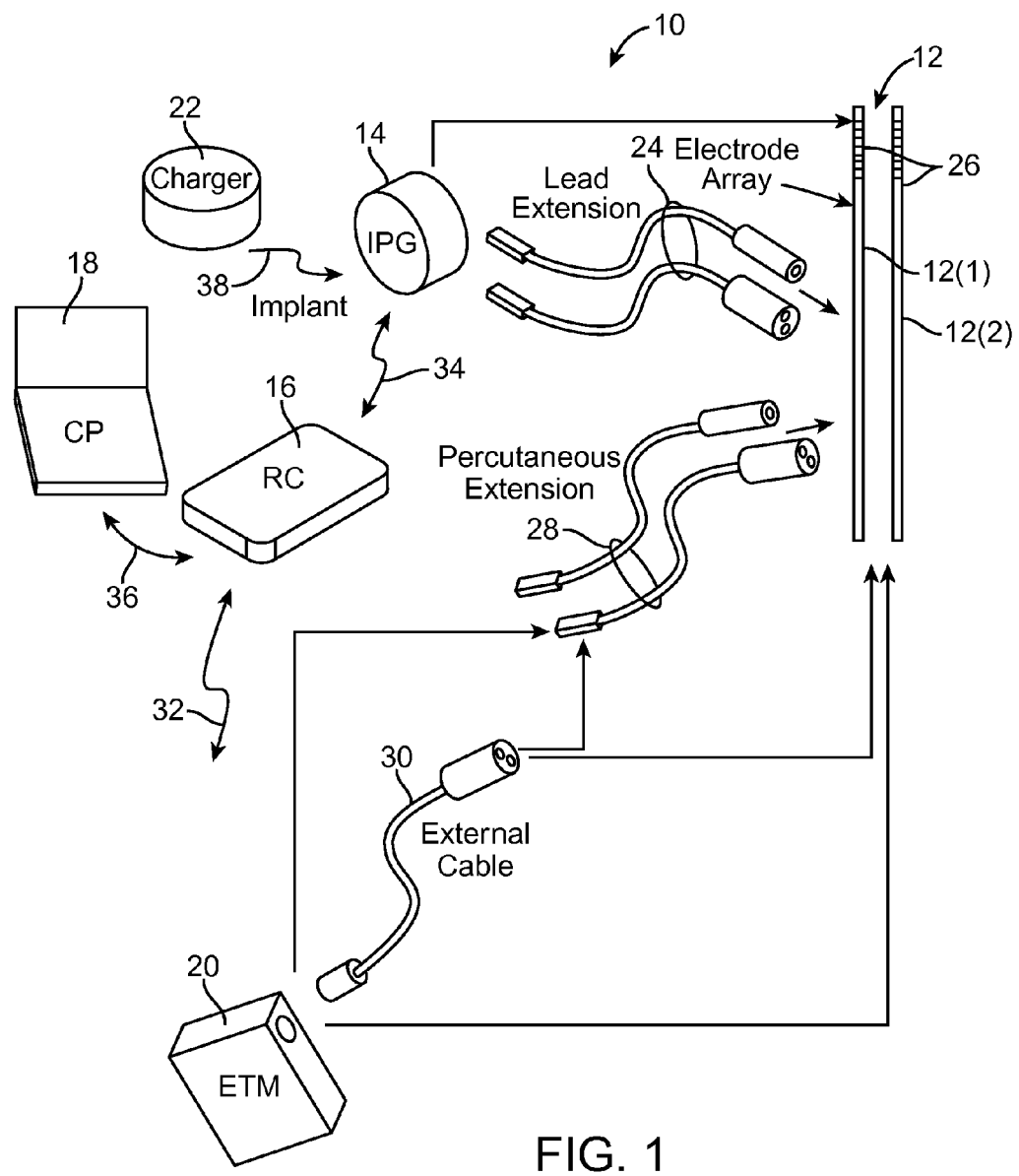
FIG. 1 is a plan view of an embodiment of a spinal cord modulation (SCM) system arranged in accordance with the present inventions.

Turning first to FIG. 1, an exemplary Spinal Cord Modulation (SCM) system 10 generally includes one or more (in this case, two) implantable modulation leads 12, an implantable pulse source (IPG) 14, an external remote controller RC 16, a clinician's programmer (CP) 18, an External Trial Modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as that of the IPG 14, also delivers electrical modulation energy in the form of a pulsed electrical waveform to the electrode array 26 in accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the stimulation that is to be provided. Thus, any functions described herein with respect to the IPG 14 can likewise be performed with respect to the ETM 20. Further details of an exemplary ETM are described in U.S. Pat. No. 6,895,280, which is expressly incorporated herein by reference.

The RC 16 may be used to telemetrically control the ETM 20 via a bi-directional RF communications link 32. Once the IPG 14 and modulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14.

The CP 18 provides clinician detailed modulation parameters for programming the IPG 14 in the operating room and in follow-up sessions. The CP 18 may perform this function by indirectly communicating with the IPG 14, through the RC 16, via an IR communications link 36. Alternatively, the CP 18 may directly communicate with the IPG 14 via an RF communications link (not shown). The clinician detailed modulation parameters provided by the CP 18 are also used to program the RC 16, so that the modulation parameters can be subsequently modified by operation of the RC 16 in a standalone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. Details of exemplary embodiments of external chargers are disclosed in U.S. Pat. No. 6,895,280, which has been previously incorporated herein by reference.

Figure 2:
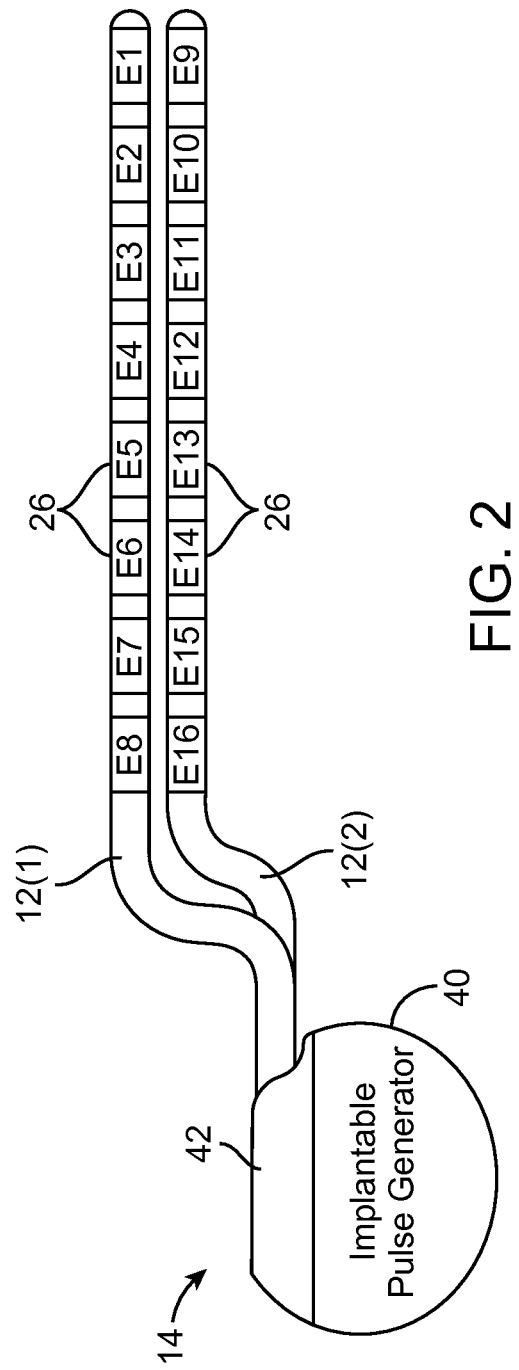
FIG. 2 is a profile view of an implantable pulse generator (IPG) used in the SCS system of FIG. 1.

Referring to FIG. 2, the IPG 14 comprises an outer case 40 for housing the electronic and other components (described in further detail below), and a connector 42 to which the proximal end of the neuromodulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

In the embodiment illustrated in FIG. 2, the neuromodulation leads 12 take the form of percutaneous leads on which the electrodes 26 (in this case, electrodes E1-E16) are disposed as ring electrodes. In the illustrated embodiment, two percutaneous leads 12(1) and 12(2) on which electrodes E1-E8 and E9-E16 are respectively disposed can be used with the SCM system 10. The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As will be described in further detail below, the IPG 14 includes pulse generation circuitry that provides electrical modulation energy to the electrodes 26 in accordance with a set of modulation parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), pulse rate (measured in pulses per second), duty cycle (pulse duration divided by cycle duration), burst rate (measured as the modulation energy on duration X and modulation energy off duration Y), and pulse shape.

With respect to the pulse patterns provided during operation of the SCM system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 40, so that the electrical current has a path from the energy source contained within the IPG case 40 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 40 of the IPG 14, so that electrical energy is transmitted between the selected electrode 26 and case 40. Monopolar delivery may also occur when one or more of the lead electrodes 26 are activated along with a large group of lead electrodes located remotely from the one or more lead electrodes 26 so as to create a monopolar effect; that is, electrical energy is conveyed from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

Figure 3:
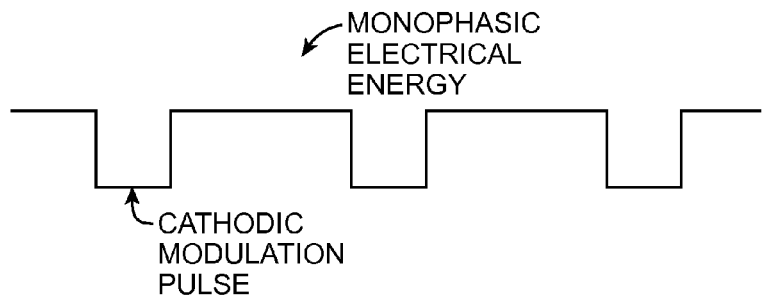
FIG. 3 is a plot of monophasic cathodic electrical stimulation energy.

The electrical energy may be delivered between a specified group of electrodes as monophasic electrical energy or multiphasic electrical energy. As illustrated in FIG. 3, monophasic electrical energy includes a series of pulses that are either all negative (cathodic), or alternatively all positive (anodic). Multiphasic electrical energy includes a series of pulses that alternate between positive and negative.

Figure 4A:
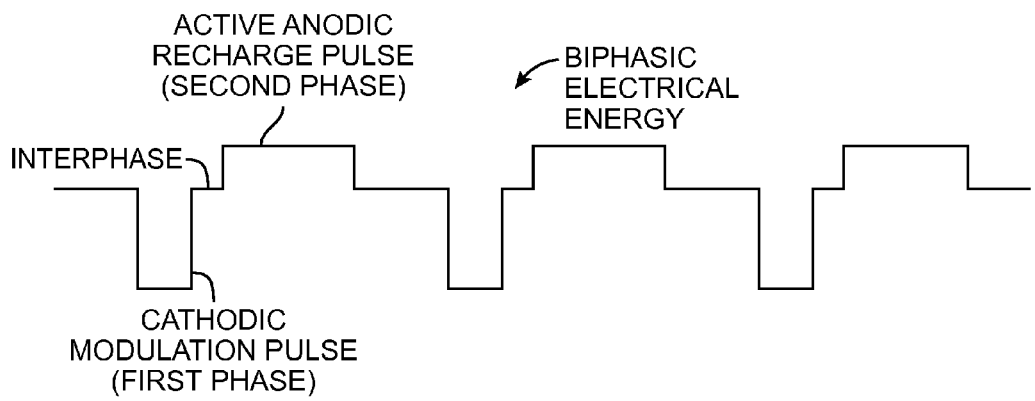
FIG. 4a is a plot of biphasic electrical stimulation energy having a cathodic stimulation pulse and an active charge recovery pulse.
Figure 4B:
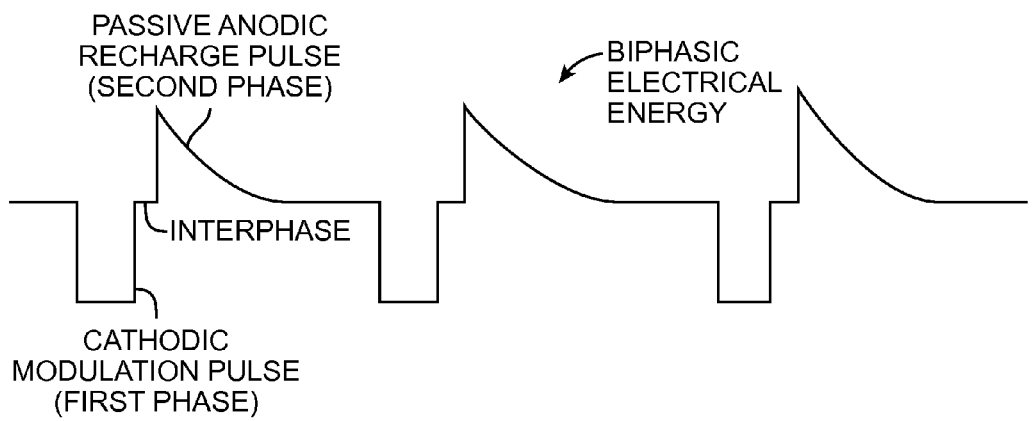
FIG. 4b is a plot of biphasic electrical stimulation energy having a cathodic stimulation pulse and a passive charge recovery pulse.

For example, as illustrated in FIGS. 4*a* and 4*b*, multiphasic electrical energy may include a series of biphasic pulses, with each biphasic pulse including a cathodic (negative) modulation pulse (during a first phase) and an anodic (positive) charge recovery pulse (during a second phase) that is generated after the modulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the charge recovery pulse).

The second phase may have an active charge recovery pulse (FIG. 4*a*), wherein electrical current is actively conveyed through the electrode via current or voltage sources, and a passive charge recovery pulse, or the second phase may have a passive charge recovery pulse (FIG. 4*b*), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds).

Figure 5:
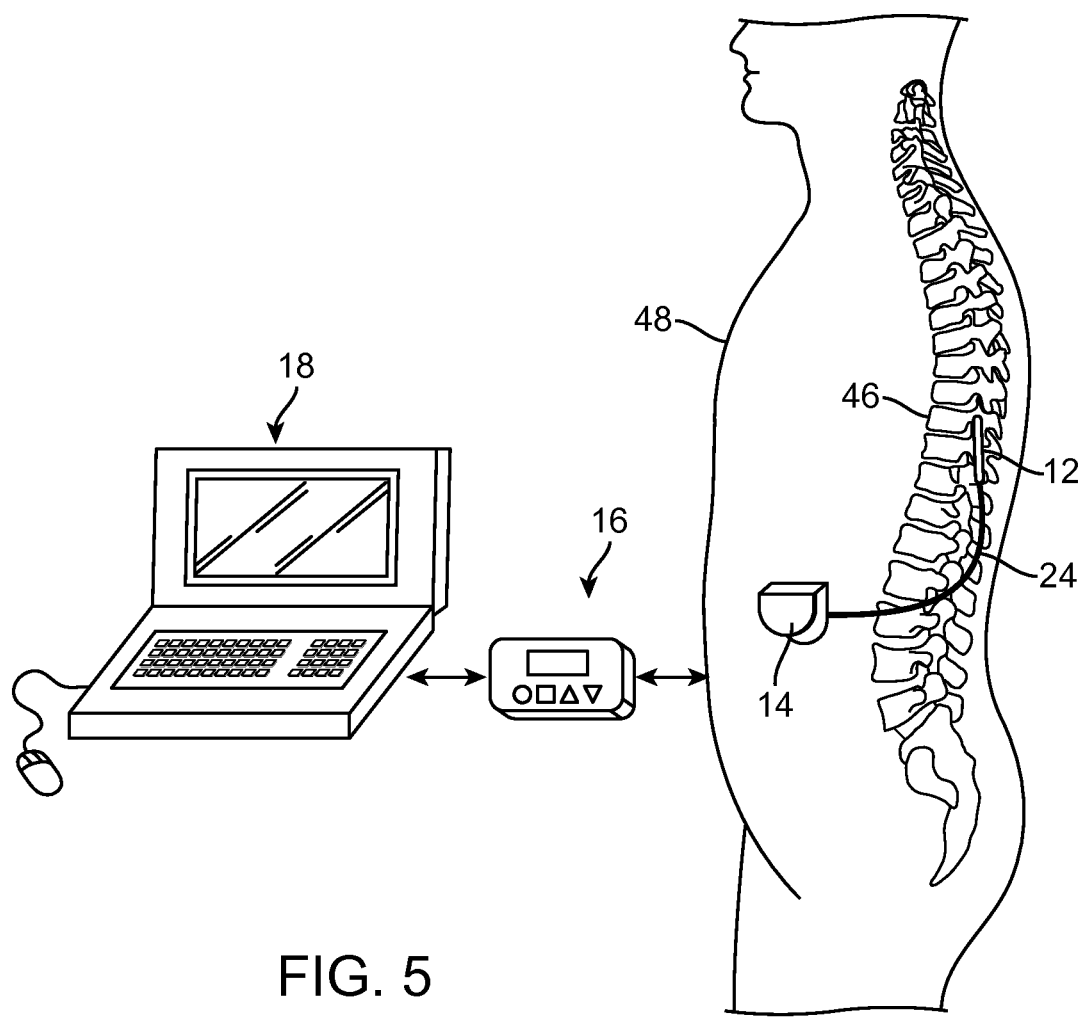
FIG. 5 is a plan view of the SCM system of FIG. 1 in use with a patient.

As shown in FIG. 5, the neuromodulation leads (or lead) 12 are implanted within the spinal column 46 of a patient 48. The preferred placement of the neuromodulation leads 12 is adjacent, i.e., resting near, or upon the dura, adjacent to the spinal cord area to be stimulated. The neuromodulation leads 12 will be located in a vertebral position that depends upon the location and distribution of the chronic pain. For example, if the chronic pain is in the lower back or legs, the neuromodulation leads 12 may be located in the mid- to low-thoracic region (e.g., at the T9-12 vertebral levels). Due to the lack of space near the location where the electrode leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Significant to the present inventions, the SCM system 10 is capable of concurrently conveying a plurality of individual electrical pulse trains respectively from a plurality of electrodes to a common electrode, thereby creating a combined electrical pulse train at the common electrode. For the purposes of this specification, electrical pulse trains are concurrently conveyed if any of their pulses overlap or are interleaved relative to each other. The combined electrical pulse train has an average pulse rate that is greater than any of the pulse rates of the individual electrical pulse trains, and preferably, an average pulse rate equal to the sum of the pulse rates. That is, the lower pulse rates at the electrodes are summed together to create a higher pulse rate at the common electrode. Significantly, this feature allows the SCM system 10 to generate electrical pulse trains at a relatively high frequency (e.g., greater than 1 KHz) that may not be achievable by utilizing an individual electrical pulse train.

In a preferred method, the individual pulse trains are respectively conveyed from the plurality of electrodes to the common electrode (or electrodes) via tissue of the patient. Preferably, the tissue adjacent the common electrode (or electrodes) is therapeutically modulated (e.g., stimulated) by the combined electrical pulse train to provide the therapy, and the tissue adjacent the plurality of electrodes is not therapeutically modulated (e.g., not stimulated) by the plurality of individual electrical pulse trains.

Figure 6:
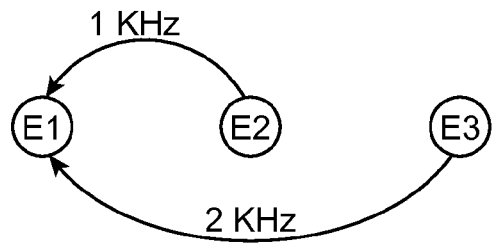
FIG. 6 is a schematic diagram showing one example of operating the implantable pulse generator of FIG. 2 to convey electrical pulse trains from a plurality of electrodes to a common electrode.
Figure 7:
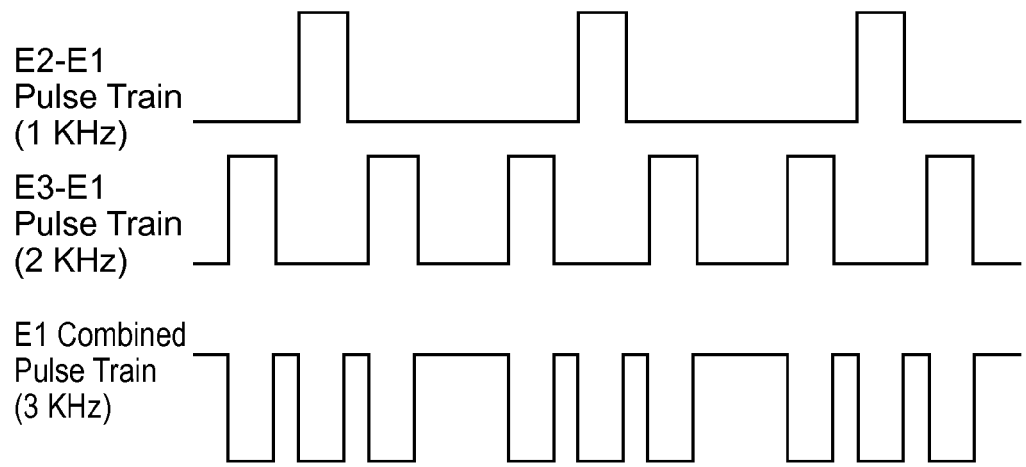
FIG. 7 is a timing diagram of one arrangement of electrical pulse trains conveyed from a plurality of electrodes to a common electrode.

For example, with reference to FIGS. 6 and 7, an electrical pulse train having a pulse rate of 1 KHz can be conveyed from electrode E2 to electrode E1, and an electrical pulse train having a pulse rate of 2 KHz can be conveyed from electrode E3 to electrode E1. As a result, a combined electrical pulse train having an average pulse rate 3 KHz can be created at electrode E1. As there shown, even though the time intervals between the pulses of the combined electrical pulse train are not uniform, the effective pulse rate of the combined electrical pulse train is 3 KHz. Although the individual electrical pulse trains conveyed from electrodes E2 and E3 are illustrated as being anodic and monophasic, and therefore, the combined electrical pulse train at electrode E1 is illustrated as being cathodic and monophasic, the individual electrical pulse trains conveyed from electrodes E2 and E3 may be cathodic and/or multiphasic, and therefore, the combined electrical pulse train at electrode E1 may be anodic and/or multiphasic.

Figure 8:
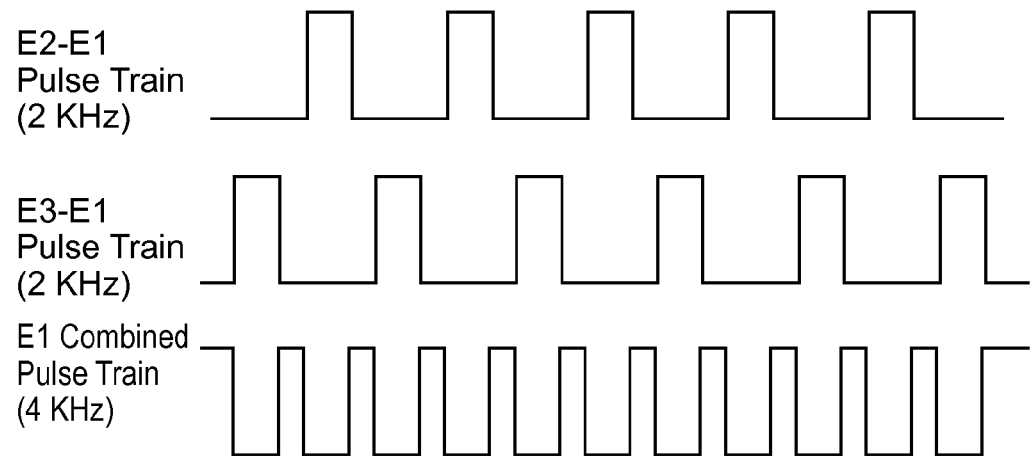
FIG. 8 is a timing diagram of another arrangement of electrical pulse trains conveyed from a plurality of electrodes to a common electrode.

Furthermore, although the individual pulse rates of the electrical pulse trains conveyed from electrodes E2 and E3 are described as being different from each other, the individual pulse rates may be identical to each other. For example, as shown in FIG. 8, an electrical pulse train having a pulse rate of 2 KHz can be conveyed from electrode E2 to electrode E1, and an electrical pulse train having a pulse rate of 2 KHz can be conveyed from electrode E3 to electrode E1. As a result, a combined electrical pulse train having an average pulse rate 4 KHz can be created at electrode E1.

Figure 9:
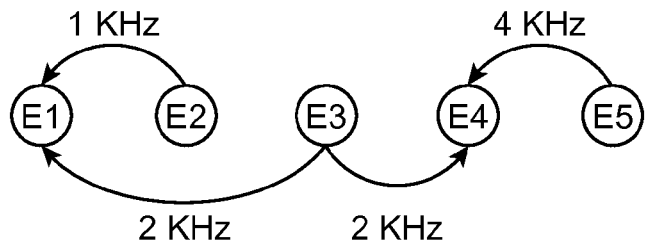
FIG. 9 is a schematic diagram showing another example of operating the implantable pulse generator of FIG. 2 to convey electrical pulse trains from a plurality of electrodes to two common electrodes.
Figure 10:
FIG. 10 is a timing diagram of an arrangement of electrical pulse trains conveyed from a plurality of electrodes to two common electrodes.
Figure 10:
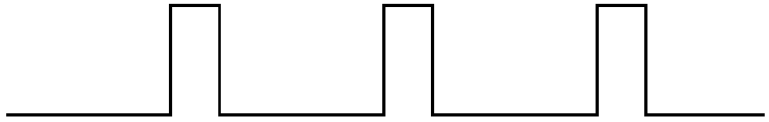
Figure 10:
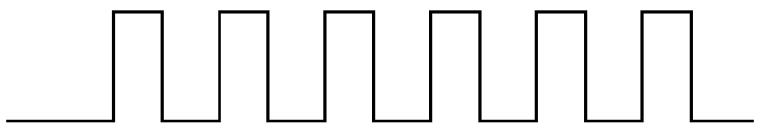
Figure 10:
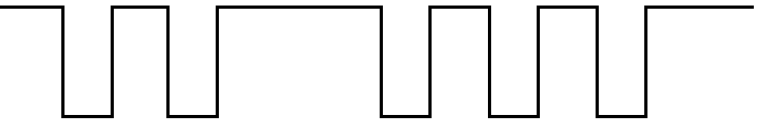
Figure 10:
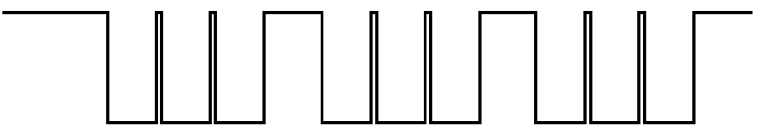

Although only a single common electrode is illustrated in FIGS. 7 and 8, electrical pulse trains can be conveyed to a plurality of common electrodes. For example, with reference to FIGS. 9 and 10, an electrical pulse train having a pulse rate of 1 KHz can be conveyed from electrode E2 to electrode E1, an electrical pulse train having a pulse rate of 2 KHz can be conveyed from electrode E3 to electrodes E1 and E4, and an electrical pulse train having a pulse rate of 4 KHz can be conveyed from electrode E5 to electrode E4. As a result, a combined electrical pulse train having an average pulse rate 3 KHz can be created at electrode E1, and another combined electrical pulse train having an average pulse rate of 6 KHz can be created at electrode E4.

Figure 11:
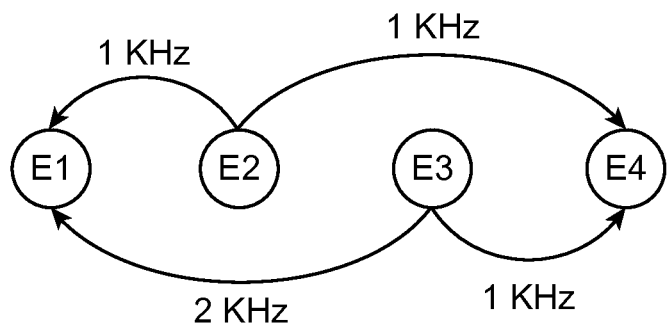
FIG. 11 is a schematic diagram showing another example of operating the implantable pulse generator of FIG. 2 to convey electrical pulse trains from a plurality of electrodes to a common electrode.
Figure 12:
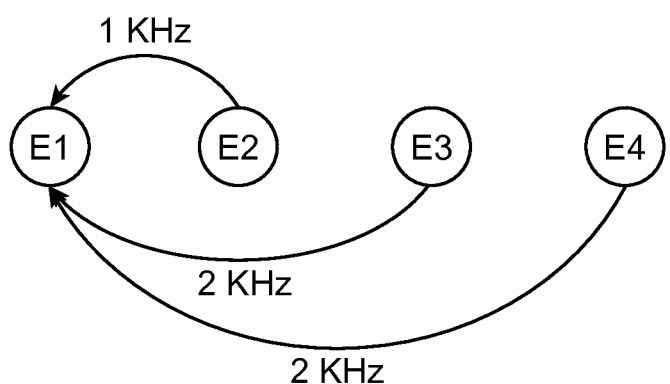
FIG. 12 is a schematic diagram showing another example of operating the implantable pulse generator of FIG. 2 to convey electrical pulse trains from a plurality of electrodes to a common electrode.

It should also be appreciated that the same electrical pulse trains can be conveyed to more than one common electrode, or a single pulse train can be conveyed from multiple electrodes. For example, as illustrated in FIG. 11, an electrical pulse train having a pulse rate of 1 KHz can be conveyed from electrode E2 to electrodes E1 and E4, and an electrical pulse train having a pulse rate of 2 KHz can be conveyed from electrode E3 to electrodes E1 and E4. As a result, a combined electrical pulse train having an average pulse rate 3 KHz can be created at both electrodes E1 and E4. As another example, as illustrated in FIG. 12, an electrical pulse train having a pulse rate of 1 KHz can be conveyed from electrode E2 to electrode E1, and an electrical pulse train having a pulse rate of 2 KHz can be conveyed from electrodes E3 and E4 to electrodes E1. It should further be appreciated that although the electrical pulse trains are bipolar in nature in that they are conveyed between two lead electrodes, any of the electrical pulse trains may be monopolar in nature by conveying the electrical pulse train to or from the case electrode.

Figure 13:
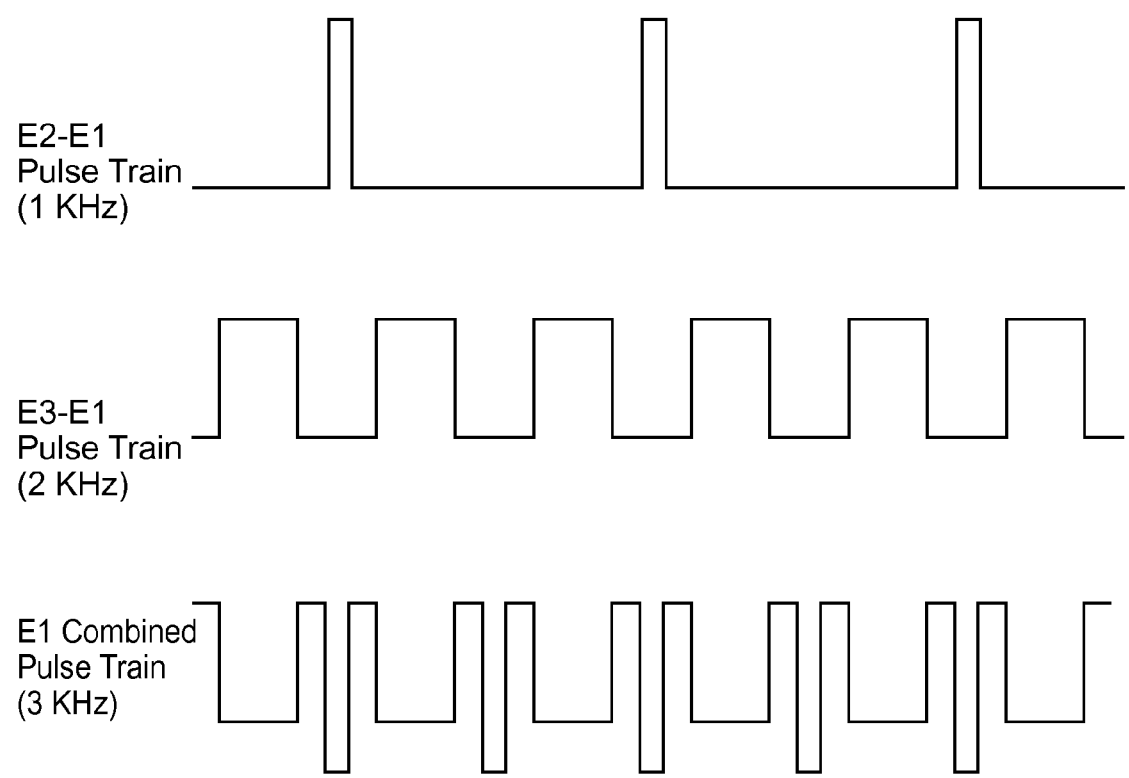
FIG. 13 is a timing diagram of an arrangement of electrical pulse trains conveyed from a plurality of electrodes to a common electrode.

Although the electrical pulse trains illustrated in FIGS. 6-12 have been described as having the same pulse amplitude, pulse duration, and pulse shape, the electrical pulse trains that are combined into a pulse train at the common electrode or electrodes may have a different pulse amplitude, pulse duration, and/or pulse shape. For example, as illustrated in FIG. 13, the electrical pulse train conveyed from electrode E2 to electrode E1 has a greater amplitude, but smaller pulse duration, then the electrical pulse train conveyed from electrode E3 to electrode E1. As a result, a combined electrical pulse train having an average pulse rate 3 KHz, with varying pulse amplitudes and pulse durations, can be created at electrode E1.

Furthermore, although the pulses of the electrical pulse trains are illustrated as being rectangular, the pulses can be other shapes, including decaying exponential shaped, increasing exponential shaped, triangularly shaped, sinusoidal shaped, or any combination of shapes. Furthermore, the shape of the pulses may be arbitrarily shaped that can be programmed. Also, although the illustrated electrical pulse trains are shown to have uniform pulse shapes, the electrical pulse trains may have different pulse shapes within a respective electrical pulse train or between electrical pulse trains. In an optional embodiment, the pulses of the electrical pulse trains may be created using a number of sinusoidal cycles.

As will be described in further detail below, the SCM system 10 may select the common electrode or electrodes in response to a user entry specifying such common electrode(s), and then select the electrodes from which the electrical pulse trains are conveyed to the common electrode(s) in response to an additional user entry specifying these electrodes. Alternatively, the SCM system 10 may automatically select the electrodes from which the electrical pulse trains are conveyed to the common electrode(s) in response to the user entry specifying the common electrode(s). For example, this selection can be accomplished randomly or in accordance with some set of heuristic rules (e.g., selecting two or more electrodes closest to the common electrode(s) or furthest from the common electrode(s)). Optionally, in response to a user entry of electrode(s) that are not desired to be used to convey electrical pulse trains, the SCM system 10 may select electrodes that do not include the undesirable electrode.

The SCM system 10 may or may not utilize arbitration when combining the individual electrical pulse trains into the combined electrical pulse train.

Figure 14:
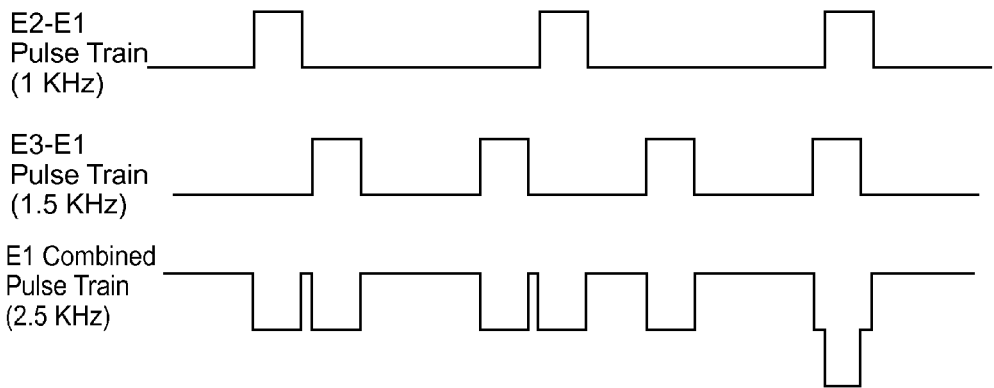
FIG. 14 is a timing diagram of an arrangement of electrical pulse trains conveyed from a plurality of electrodes to a common electrode without using arbitration.

If the SCM system 10 does not utilize arbitration, the pulses of each respective individual electrical pulse train may be uniformly spaced while allowing the pulses of the individual pulse trains to temporally overlap each other, as illustrated in FIG. 14. In the case where there is no arbitration, the maximum time interval between any two pulses in the combined electrical pulse train will be limited by the highest pulse rate of the individual electrical pulse trains, whereas the minimum time interval between any two pulses in the combined electrical pulse train will be as zero (overlapping pulses edge to edge). Notably, if the greatest common divisor of the periods of the individual electrical pulse trains is equal to or greater than the sum of the pulse durations of the individual electrical pulse trains, the pulses of the electrical pulse trains can be interleaved in a manner that will preserve the uniform spacing between the pulses of each electrical pulse train will preventing overlap between the pulses, as described in U.S. patent application Ser. No. 12/550,185, entitled "Methods to Avoid Frequency Locking in a Multi-Channel Neurostimulation System Using a Greatest Common Divisor Rule," which is expressly incorporated herein by reference.

If the SCM system 10 utilizes arbitration, the pulses of at least one of the electrical pulse trains are variably spaced from each other in a manner that limits the time intervals between the pulses of the combined electrical pulse train to a minimum time interval, which can be as small as zero.

Figure 15:
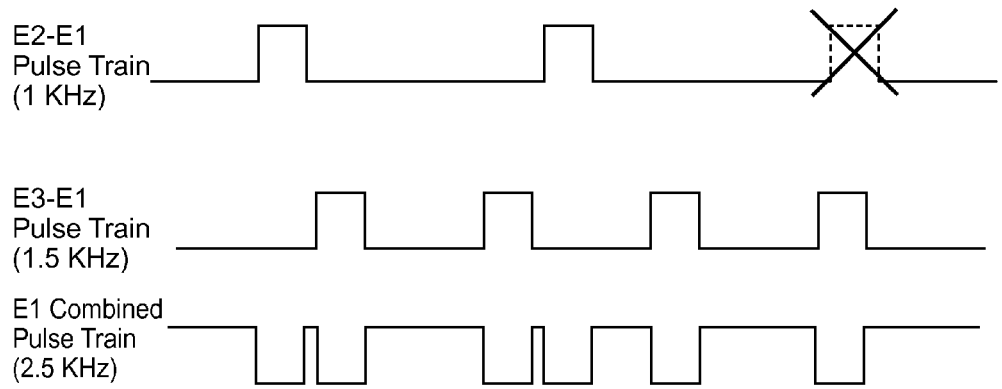
FIG. 15 is a timing diagram of an arrangement of electrical pulse trains conveyed from a plurality of electrodes to a common electrode using one arbitration technique.

For example, as illustrated in FIG. 15, a pulse of one of the individual pulse trains that will potentially overlap temporally (or otherwise violate the minimum time interval) with a pulse of another of the individual pulse train (as shown in phantom) may be dropped or cancelled to prevent such overlap or minimum time interval violation. Further details discussing this technique are described in U.S. patent application Ser. No. 12/550,237, entitled "Method to Avoid Frequency Locking in a Multi-Channel Neurostimulation System Using Pulse Placement," which is expressly incorporated herein by reference.

Figure 16:
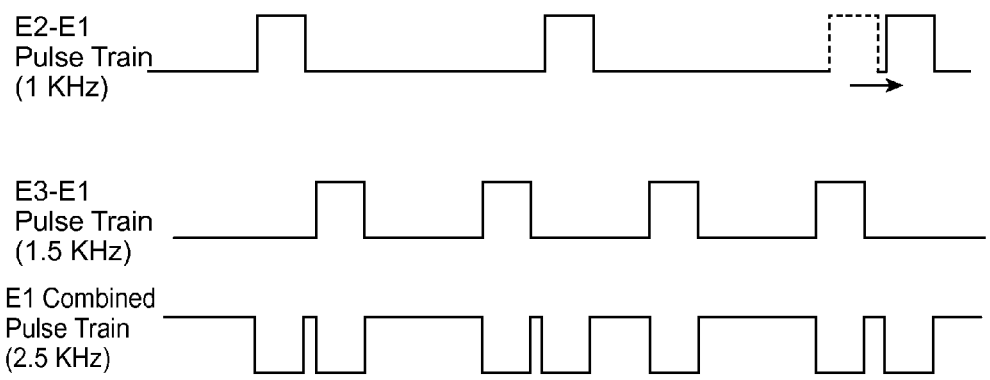
FIG. 16 is a timing diagram of an arrangement of electrical pulse trains conveyed from a plurality of electrodes to a common electrode using another arbitration technique.

In another example, as illustrated in FIG. 16, a pulse of one of the individual pulse trains that will potentially overlap temporally (or otherwise violate the minimum time interval) with a pulse of another of the individual pulse train (as shown in phantom) may be shifted to prevent such overlap or minimum time interval violation. Further details discussing this technique are described in U.S. patent application Ser. No. 12/550,237, entitled "Method to Avoid Frequency Locking in a Multi-Channel Neurostimulation System Using Pulse Shifting," which is expressly incorporated herein by reference.

Notably, the individual electrical pulse train in which a pulse is cancelled or shifted can be selected in accordance with any criteria. For example, a pulse of one individual electrical pulse train that potentially overlaps or violates the minimum time interval with a pulse of another individual electrical pulse train that has already occurred may be selected to be cancelled or shifted. As another example, the individual electrical pulse trains may be prioritized, such that the individual electrical pulse train with the lowest priority relative to other electrical pulse trains is selected to have its pulse cancelled or shifted. Such priority may be based on, e.g., the pulse having the lowest pulse amplitude, lowest pulse duration, lowest injected charge, or lowest injected charged density, with the individual electrical pulse train having the lowest of these parameters selected to have its potentially overlapping pulse cancelled or shifted. In other embodiments, the arbitration rules allow overlap or violation of the minimum time interval between pulses of respective electrical pulse trains if the summation of the pulses does not exceed a maximum pulse amplitude, maximum pulse duration, maximum injected charge, or maximum injected charged density.

In the case where the pulses are biphasic, the arbitration rules may ensure that both phases of each biphasic pulse are completed before any phase of the next biphasic pulse is conveyed. Alternatively, the arbitration rules may allow for the modulation phases for multiple biphasic pulses to be conveyed before the charge recovery phases of these multiple biphasic pulses. For example, the arbitration rules may also for two or more cathodic phases before any anodic phase occurs. In one embodiment, the arbitration rules allows for particular phases of the biphasic pulses to overlap while preventing the other phases of the biphasic pulses from overlapping each other. Optionally, there may be arbitration rules for maximum pulse width and maximum amplitude (not only frequency) can be provided, so that the combined electrical pulse train may have a limit to the maximum frequency, maximum pulse width, and/or maximum amplitude that limit charge injection for pulse to a maximum level or average charge injection per second to a given level.

Optionally, the each of the electrical pulse trains may be generated in accordance with a cyclically varying set of modulation parameters, such that the combined electrical pulse train has a cyclically varying set of modulation parameters. The electrical pulse trains may also be repeatedly generated in a bursting pattern. For the purposes of this specification, cycling refers to sequences of pulses that are executed in a regular fashion, whereas bursting patterns refer to a limited duration event (such as a bolus or limited duration sequence). Different phases of cycling can refer to different pulse rates, electrode combinations, pulse amplitudes, pulse duration, injected charge, injected charge density or even on-off periods of modulation. The cycling and bursting patterns can be applied to only one individual electrical pulse trains or all of the electrical pulse trains, and can be different between the individual electrical pulse trains. The cycling and bursting patterns may include different frequencies for the different cycle and burst phases. The cycling and bursting pattern can have a phase with a given frequency and a phase with a different frequency. One phase can have a pulse rate of 1 KHz and higher, while another phase can have a pulse rate of less than 1 KHz. In one preferred embodiment, the cycling and burst patterns can include phases as short as 0.5 ms and as large as one week. In an optional embodiment, secondary cycling patterns can be used one on top of the other in any given individual electrical pulse train or combination of electrical pulse trains. For example, the first cycling pattern can create a pattern of two phases (each one lasting less than one hour), and the second cycling pattern may have phases that are longer than the first cycling (for example, phases of 24 hours).

In another optional embodiment, the modulation parameters in accordance with which the electrical pulse trains are conveyed may be modified based on the posture or activity of the patient. In one particular technique, the individual electrical pulse trains may be combined to create a combined electrical pulse train with a relatively high pulse rate, which then switches to a relatively low pulse rate (or even off-status) when the SCM system 10 detects that the patient is laying down, or after a programmable time (e.g., 30 minutes), after laying down for a period of time, thereby reducing the power consumption.

Figure 17:
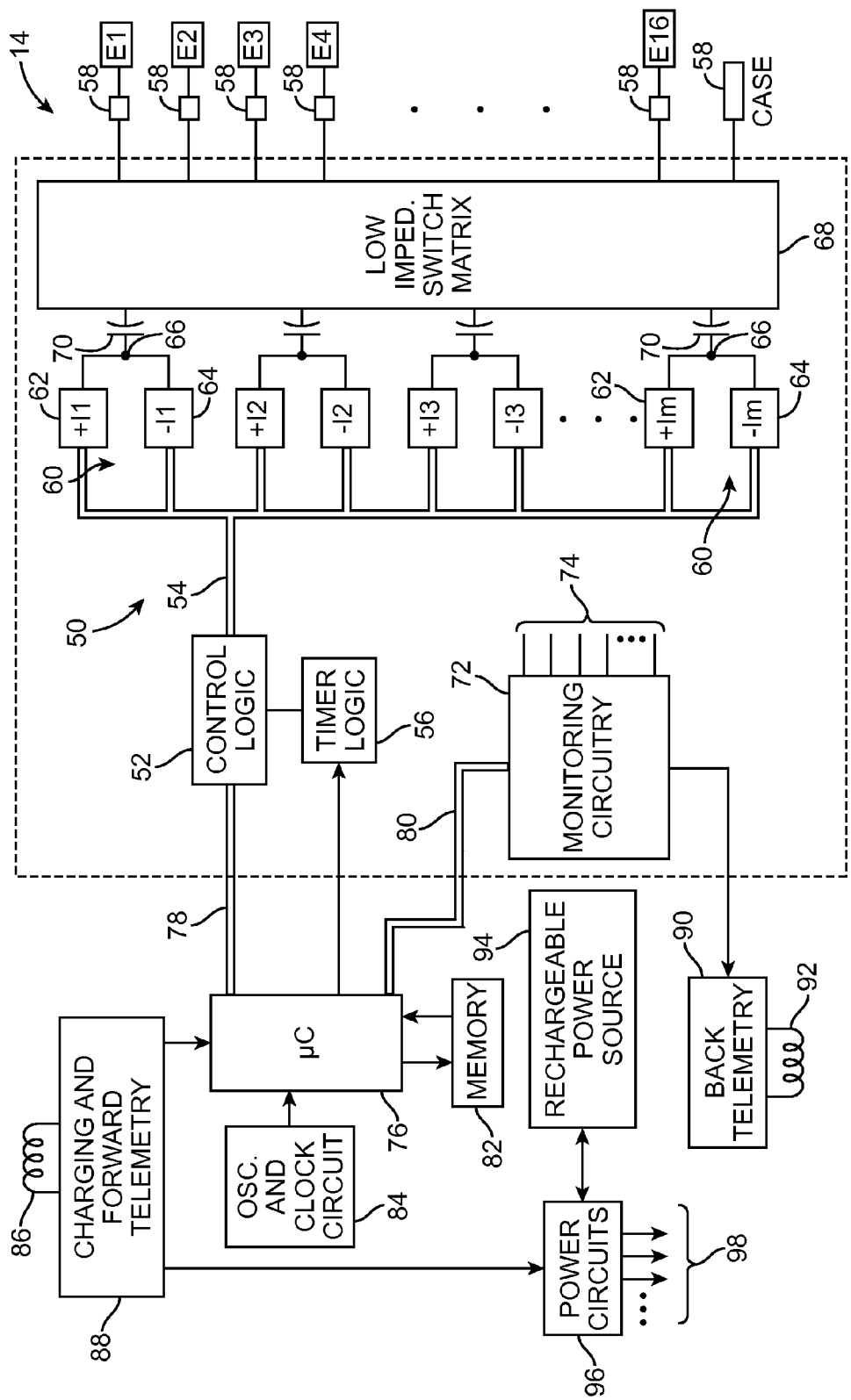
FIG. 17 is a block diagram of the internal components of the IPG of FIG. 2.

Turning next to FIG. 17, the main internal components of the IPG 14 will now be described. The IPG 14 includes modulation output circuitry 50 configured for generating electrical modulation energy in accordance with a defined pulsed waveform having a specified pulse amplitude, pulse rate, pulse duration, and pulse shape under control of control logic 52 over data bus 54. Control of the pulse rate and pulse duration of the electrical waveform is facilitated by timer logic circuitry 56, which may have a suitable resolution, e.g., 10 μs. The electrical modulation energy generated by the modulation output circuitry 50 is output to electrical terminals 58 corresponding to electrodes E1-E16.

The modulation output circuitry 50 may either comprise one or more independently controlled electrical sources, which take the form of current sources and/or current sinks, for providing stimulation pulses of a specified and known amperage to or from the electrodes 26, or voltage sources and/or voltage sinks for providing stimulation pulses of a specified and known voltage at the electrodes 26. The current (or voltage) sources or sinks include constant current (or voltage) sources and associated analog switches to generate the electrical pulse trains.

For example, in the illustrated embodiment, the modulation output circuitry 50 comprises a plurality m independent current source pairs 60 capable of supplying electrical modulation energy to the electrical terminals 58 at a specified and known amperage. One current source 62 of each pair 60 functions as a positive (+) or anodic current source, while the other current source 64 of each pair 60 functions as a negative (−) or cathodic current source. The outputs of the anodic current source 62 and the cathodic current source 64 of each pair 60 are connected to a common node 66.

In essence, each current source pair 60 takes the form of a reconfigurable current source whose polarity can be switched. That is, by activating the anodic current source 62 and deactivating the cathodic current source 64, the current source pair 60 can be configured as an anodic current source, and by deactivating the anodic current source 62 and activating the cathodic current source 64, the current source pair 60 can be configured as a cathodic current source.

The modulation output circuitry 50 further comprises a low impedance switching matrix 68 through which the common node 66 of each current source pair 60 is connected to any of the electrical terminals 58, and a capacitor 70 coupled between the common node 66 of each current source pair 60 and the switching matrix 68. Thus, as briefly discussed above, the switching matrix 68 can be operated to concurrently convey a plurality of electrical pulse trains respectively from a plurality of electrical terminals 58 (and the corresponding electrodes) to a common electrical terminal or terminals (and the corresponding electrode(s)), thereby creating a combined electrical pulse rate having an average pulse rate greater than any of the pulse rates of the individual electrical pulse trains.

Hence, it is seen that each of the programmable electrical terminals 58 can be programmed to have a positive (sourcing current), a negative (sinking current), or off (no current) polarity. Further, the amplitude of the current pulse being sourced or sunk to or from a given electrode may be programmed to one of several discrete current levels, e.g., between 0 to 10 mA in steps of 100 μA, within the output voltage/current requirements of the IPG 14. Additionally, in one embodiment, the total current output by a group of electrical terminals 58 can be up to ±20 mA (distributed among the electrodes included in the group). Also, the pulse duration of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 5000 pulses per second (pps). Other programmable features can include slow start/end ramping, burst stimulation cycling (on for X time, off for Y time), interphase (i.e., the duration between first and second phases of biphasic energy), and open or closed loop sensing modes. Moreover, it is seen that each of the electrical terminals 58 can operate in a multipolar mode, e.g., where two or more electrical terminals are grouped to source/sink current at the same time. Alternatively, each of the electrical terminals 58 can operate in a monopolar mode where, e.g., the electrical terminals 58 are configured as cathodes (negative), and case of the IPG 14 is configured as an anode (positive).

It can be appreciated that an electrical terminal 58 may be assigned an amplitude and included with any of up to k possible groups, where k is an integer corresponding to the number of channels, and in one embodiment, is equal to 4, and with each channel k having a defined pulse amplitude, pulse duration, pulse rate, and pulse shape. Other channels may be realized in a similar manner. Thus, each channel identifies which electrical terminals 58 (and thus electrodes) are selected to synchronously source or sink current, the pulse amplitude at each of these electrical terminals, and the pulse duration, pulse rate, and pulse shape. The individual electrical pulse trains that are concurrently generated to create the combined electrical pulse train can be respectively conveyed in the k number of channels. Amplitudes and polarities of electrodes on a channel may vary, e.g., as controlled by the RC 16. External programming software in the CP 18 is typically used to set modulation parameters including electrode polarity, amplitude, pulse rate and pulse duration for the electrodes of a given channel, among other possible programmable features.

The operation of this output stimulation circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 further comprises monitoring circuitry 72 for monitoring the status of various nodes or other points 74 throughout the IPG 14, e.g., power supply voltages, temperature, battery voltage, and the like. Notably, the electrodes 26 fit snugly within the epidural space of the spinal column, and because the tissue is conductive, electrical measurements can be taken between the electrodes 26. Thus, the monitoring circuitry 72 is configured for taking such electrical measurements (e.g., current output magnitude, electrode impedance, field potential, evoked action potentials, etc.) for performing such functions as detecting fault conditions between the electrodes 26 and the modulation output circuitry 50, determining the coupling efficiency between the electrodes 26 and the tissue, facilitating lead migration detection, etc. In the case where voltage sources (instead of current sources) are used, the monitoring circuitry 72 can measure the impedances on the electrodes 26 in order to maintain a desired current distribution on the active electrodes 26 by adjusting the voltages on the active electrodes 26. Furthermore, whether current sources or voltage sources are used, the monitoring circuitry 72 will be used to measure impedances for ensuring that the actual current values best match the desired current values on the electrodes, as will be discussed in further detail below.

The IPG 14 further comprises processing circuitry in the form of a microcontroller (μC) 76 that controls the control logic over data bus 78, and obtains status data from the monitoring circuitry 72 via data bus 80. The IPG 14 additionally controls the timer logic 56 and switching matrix 68. The IPG 14 further comprises memory 82 and oscillator and clock circuitry 84 coupled to the microcontroller 76. The microcontroller 76, in combination with the memory 82 and oscillator and clock circuit 84, thus comprise a microprocessor system that carries out a program function in accordance with a suitable program stored in the memory 82. Alternatively, for some applications, the function provided by the microprocessor system may be carried out by a suitable state machine.

Thus, the microcontroller 76 generates the necessary control and status signals, which allow the microcontroller 76 to control the operation of the IPG 14 in accordance with a selected operating program and modulation parameters. In controlling the operation of the IPG 14, the microcontroller 76 is able to individually generate the individual electrical pulse trains at the electrodes 26 using the modulation output circuitry 50, in combination with the control logic 52 and timer logic 56, thereby activating selected ones of the electrodes 26, including the monopolar case electrode. In accordance with modulation parameters stored within the memory 82, the microcontroller 76 may control the polarity, amplitude, rate, pulse duration and channel through which the current modulation pulses are provided. The microcontroller 76 also facilitates the storage of electrical parameter data (or other parameter data) measured by the monitoring circuitry 72 within memory 82, and also provides any computational capability needed to analyze the raw electrical parameter data obtained from the monitoring circuitry 72 and compute numerical values from such raw electrical parameter data.

The IPG 14 further comprises an alternating current (AC) receiving coil 86 for receiving programming data (e.g., the operating program and/or modulation parameters) from the RC 16 and/or CP 18 (shown in FIG. 5) in an appropriate modulated carrier signal, and charging and forward telemetry circuitry 88 for demodulating the carrier signal it receives through the AC receiving coil 86 to recover the programming data, which programming data is then stored within the memory 82, or within other memory elements (not shown) distributed throughout the IPG 14.

The IPG 14 further comprises back telemetry circuitry 90 and an alternating current (AC) transmission coil 92 for sending informational data sensed through the monitoring circuitry 72 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18. The back telemetry features allow raw or processed electrical parameter data (or other parameter data) previously stored in the memory 82 to be downloaded from the IPG 14 to the RC 16 and/or CP 18.

The IPG 14 further comprises a rechargeable power source 94 and power circuits 96 for providing the operating power to the IPG 14. The rechargeable power source 94 may, e.g., comprise a lithium-ion or lithium-ion polymer battery. The rechargeable battery 94 provides an unregulated voltage to the power circuits 96. The power circuits 96, in turn, generate the various voltages 98, some of which are regulated and some of which are not, as needed by the various circuits located within the IPG 14. The rechargeable power source 94 is recharged using rectified AC power (or DC power converted from AC power through other means, e.g., efficient AC-to-DC converter circuits, also known as "inverter circuits") received by the AC receiving coil 86. To recharge the power source 94, the external charger 22 (shown in FIG. 1), which generates the AC magnetic field, is placed against, or otherwise adjacent, to the patient's skin over the implanted IPG 14. The AC magnetic field emitted by the external charger induces AC currents in the AC receiving coil 86. The charging and forward telemetry circuitry 88 rectifies the AC current to produce DC current, which is used to charge the power source 94. While the AC receiving coil 86 is described as being used for both wirelessly receiving communications (e.g., programming and control data) and charging energy from the external device, it should be appreciated that the AC receiving coil 86 can be arranged as a dedicated charging coil, while another coil can be used for bi-directional telemetry.

It should be noted that the diagram of FIG. 17 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Source," which are expressly incorporated herein by reference. It should be noted that rather than an IPG, the SCM system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As briefly discussed above, the IPG 14 may be programmed to control the conveyed electrical energy in accordance with the set of modulation parameters. More significant to the present inventions, the RC 16 and/or CP 18 may include a user interface in which user commands are input to specify the electrode or electrodes from which high frequency electrical energy will be delivered.

In particular, in one embodiment, the user interface receives an input from a user specifying the common electrode or electrodes 26 (and corresponding common electrical terminal or terminals 58) to which the individual electrical pulse trains is conveyed to create the high frequency electrical energy at the common electrode or electrodes 26, and control circuitry (which may be the microcontroller 76 or the controller in the RC 16 and/or CP 18) may select the common electrode or electrodes 26 in response to this user input. The control circuitry may also automatically select the electrodes 26 from which the individual electrical pulse trains are conveyed in response to this user input.

Alternatively, user commands specifying the electrodes from which the individual electrical pulse trains are conveyed can be entered into the user interface, and the control circuitry may select these electrodes 26 to convey these individual electrical pulse trains in response to this user input. Optionally, user commands specifying the electrodes from which the individual electrical pulse trains are not be conveyed can be entered into the user interface, and the control circuitry may select electrodes 26, which do not include the user specified electrodes, from which the individual electrical pulse trains are conveyed in response to this user input.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method comprising:
    treating chronic pain using a plurality of electrodes, including providing a high-frequency neuromodulation therapy to therapeutically modulate a volume of spinal cord tissue to treat chronic pain without causing paresthesia, the plurality of electrodes including a common electrode and at least two electrodes different than the common electrode,
    wherein providing the high-frequency neuromodulation therapy includes:
        placing the common electrode adjacent to the volume of spinal cord tissue to be therapeutically modulated to treat chronic pain; and
        delivering a combined electrical pulse train having an average pulse rate equal to or greater than 1 KHz, wherein delivering the combined electrical pulse train includes respectively delivering at least two electrical pulse trains from the at least two electrodes to the common electrode to provide the combined electrical pulse train from the common electrode to the volume of tissue to be modulated to treat chronic pain without causing paresthesia, wherein each of the at least two electrical pulse trains are concurrently delivered to the common electrode and have an average pulse rate less than the average pulse rate of the combined electrical pulse train.

2. The method of claim 1, wherein the average pulse rate of the combined electrical pulse train is less than 50 KHz.

3. The method of claim 1, wherein the combined electrical pulse train at the common electrical terminal is anodic.

4. The method of claim 1, wherein the average pulse rate of the combined electrical pulse train is equal to the sum of pulse rates for the at least two electrical pulse trains.

5. The method of claim 1, wherein the at least two electrical pulses trains have identical pulse rates.

6. The method of claim 1, wherein the at least two electrical pulse trains have pulse rates that differ from each other.

7. The method of claim 1, wherein the plurality of electrodes include another common electrode and another at least two electrodes, the method further comprising placing the other common electrode adjacent to the volume of spinal cord tissue to be therapeutically modulated, and delivering another combined electrical pulse train at the other common electrode, the other combined electrical pulse train having another average pulse rate greater than 1 KHz, wherein delivering the other combined electrical pulse train includes concurrently delivering at least two electrical pulse trains from the other at least two of electrodes to the other common electrode.

8. The method of claim 1, wherein the electrical pulse trains are generated using a single electrical source.

9. The method of claim 1, wherein the electrical pulse trains are generated using a plurality of electrical sources.

10. The method of claim 1, further comprising receiving an input from a user, via a user interface, identifying the common electrode.

11. The method of claim 10, wherein further comprising automatically selecting the at least two electrodes in response to the input from the user identifying the common electrode.

12. The method of claim 10, further comprising receiving an input from the user specifying the at least two electrodes.

13. The method of claim 10, further comprising receiving an input from the user specifying an electrode to be excluded, wherein selecting the at least two electrodes excludes the electrode to be excluded specified by the user.

14. The method of claim 1, wherein the at least two electrical pulse trains have different values for a modulation parameter that comprises one of a pulse amplitude, pulse duration, and pulse shape.

15. The method of claim 1, further comprising uniformly spacing pulses of each respective individual electrical pulse train from each other.

16. The method of claim 1, wherein further comprising variably spacing pulses of at least one of the electrical pulse trains in a manner that limits the time intervals between the pulses of the combined electrical pulse train to a minimum time interval.

17. The method of claim 1, wherein at least one pulse in each of the plurality of individual electrical pulse trains is multiphasic.

18. The method of claim 1, further comprising generating each of the individual electrical pulse trains in accordance with a cyclically varying set of modulation parameters.

19. The method of claim 1, wherein further comprising repeatedly generating the electrical pulse trains in a bursting pattern.

20. A method, comprising:
    treating chronic pain using a plurality of electrodes, including providing a high-frequency neuromodulation therapy to therapeutically modulate a volume of spinal cord tissue to treat chronic pain without causing paresthesia, the plurality of electrodes including a first common electrode and a second common electrode and a first group of at least two electrodes different than the first common electrode and a second group of at least two electrodes different than the second common electrode,
    wherein providing the high-frequency neuromodulation therapy includes:
        placing the first common electrode adjacent to the volume of spinal cord tissue to be therapeutically modulated and placing the second common electrode adjacent to the volume of spinal cord tissue to be therapeutically modulated;
        delivering both a first combined electrical pulse train and a second combined electrical pulse train where each has an average pulse rate equal to or greater than 1, wherein delivering the first combined electrical pulse train includes respectively delivering at least two electrical pulse trains from the first group of at least two electrodes to the first common electrode to provide the first combined electrical pulse train from the first common electrode to the volume of spinal cord tissue to be modulated, wherein delivering the second combined electrical pulse train includes respectively delivering at least two electrical pulse trains from the second group of at least two of electrodes to the second common electrode to provide the second combined electrical pulse train from the second common electrode to the volume of spinal cord tissue to be modulated wherein each of the at least two electrical pulse trains of each group are concurrently delivered to their respective common electrode and each have an average pulse rate less than the average pulse rate of each respective combined electrical pulse train, wherein each of the individual electrical pulse trains is generated in accordance with a cyclically varying set of modulation parameters, and wherein the first and second combined electrical pulse trains for the high-frequency neuromodulation therapy are used to block or otherwise disrupt naturally occurring action potentials within neural fibers to treat chronic pain without causing paresthesia.

\* \* \* \* \*